US011260385B2

(12) United States Patent
Hansen et al.

(10) Patent No.: US 11,260,385 B2
(45) Date of Patent: Mar. 1, 2022

(54) LAMINAR AIR FLOW WORKSTATION WITH TEMPERATURE CONTROL

(71) Applicant: Kivex Biotec A/S, Birkerød (DK)

(72) Inventors: Niels Stengaard Hansen, Birkerød (DK); Thomas Grau-Andersen, Birkerød (DK); Torben Henning Ingemannsen, Birkerød (DK)

(73) Assignee: Kivex Biotec A/S, Birkerød (DK)

( * ) Notice: Subject to any disclaimer, the term of this patent is extended or adjusted under 35 U.S.C. 154(b) by 540 days.

(21) Appl. No.: 15/774,527

(22) PCT Filed: Oct. 26, 2016

(86) PCT No.: PCT/IB2016/056437
§ 371 (c)(1),
(2) Date: May 8, 2018

(87) PCT Pub. No.: WO2017/081572
PCT Pub. Date: May 18, 2017

(65) Prior Publication Data
US 2020/0261900 A1    Aug. 20, 2020

(30) Foreign Application Priority Data
Nov. 9, 2015   (DK) .............. PA 2015 70718

(51) Int. Cl.
*B01L 1/04*     (2006.01)
*B08B 15/02*    (2006.01)
*F24F 3/163*    (2021.01)

(52) U.S. Cl.
CPC .............. *B01L 1/04* (2013.01); *B08B 15/023* (2013.01); *F24F 3/163* (2021.01); *B01L 2300/18* (2013.01)

(58) Field of Classification Search
CPC ........ B08B 15/023; F24F 3/1607; F24F 3/161; F24F 2003/1639; F24F 3/163; B01L 2300/18
(Continued)

(56) References Cited

U.S. PATENT DOCUMENTS 3,745,908 A * 7/1973 Mayberry ............ B08B 15/023
454/57
3,752,056 A   8/1973 Chamberlin et al.
(Continued)

FOREIGN PATENT DOCUMENTS

DE   36 32 276    4/1987
DE   3632276      4/1987 ............. F24F 3/00
(Continued)

OTHER PUBLICATIONS

The International Search Report for International Application No. PCT/IB2016/056437 dated Dec. 22, 2016.
(Continued)

*Primary Examiner* — Edelmira Bosques
*Assistant Examiner* — Ryan L Faulkner
(74) *Attorney, Agent, or Firm* — Fish & Richardson P.C.

(57) ABSTRACT

Laminar air flow workstation, comprising: a working chamber (1) comprising a work table (2), an air circulation system (3) comprising first heating means (4), and configured to circulate heated air in the workstation and direct a heated and temperature controlled air flow towards the work table (2), wherein the working chamber comprises a front handling opening (6) in fluid connection with the surroundings (7), and configured such that the work table (2) can be accessed from the surroundings (7). Also disclosed are the use of the workstation for handling and/or microscopy of biological materials, such as tissue, embryos, and stem cells,
(Continued)

as well as the use of the workstation for microbiological safety workstation in accordance with ISO/EN 12469.

19 Claims, 5 Drawing Sheets

(58) Field of Classification Search
USPC .......................................................... 454/52
See application file for complete search history.

(56) References Cited

U.S. PATENT DOCUMENTS

| | | | |
|---|---|---|---|
| 3,925,043 A * | 12/1975 | Matrone | |
| 4,202,676 A * | 5/1980 | Pelosi, Jr. ............. | A61G 13/108 |
| | | | 422/120 |
| 5,083,558 A * | 1/1992 | Thomas ................. | A61G 10/02 |
| | | | 128/202.12 |
| 5,761,908 A * | 6/1998 | Oas ....................... | F24F 12/006 |
| | | | 62/3.2 |
| 10,507,500 B1 * | 12/2019 | Hunter .................. | B08B 15/023 |
| 2008/0150404 A1 | 6/2008 | Ono | |
| 2009/0318751 A1 | 12/2009 | Lansdowne | |

FOREIGN PATENT DOCUMENTS

| | | | | |
|---|---|---|---|---|
| EP | 2 399 682 | 12/2011 | | |
| GB | 1 275 491 | 5/1972 | | |
| JP | H05-256486 | 10/1993 | ................ | F24F 7/06 |
| JP | H 06-121935 | 5/1994 | | |
| JP | H06-121935 | 5/1994 | ................ | B01L 1/00 |
| JP | 2002-364896 | 12/2002 | ................ | F24F 7/06 |
| JP | 2007-255854 | 10/2007 | ................ | F24F 7/06 |
| JP | 2008-149290 | 7/2008 | ................ | B01L 1/00 |
| JP | 2008-200671 | 9/2008 | ................ | B01L 1/00 |
| JP | 2008-307496 | 12/2008 | ................ | B01L 1/00 |
| JP | 2009-119391 | 6/2009 | ................ | B01L 1/00 |
| JP | 2013-085994 | 5/2013 | ................ | B01L 1/00 |
| WO | WO 2006/125980 | 11/2006 | | |

OTHER PUBLICATIONS

International Preliminary Report on Patentability for International Application No. PCT/IB2016/056437 dated May 24, 2018.
The Chinese First Office Action for Chinese Application No. CN 201680065390.8 dated Jul. 24, 2020.
The Japanese Office Action for Japanese Application No. JP 2018-543468 dated Jul. 8, 2019.
Kivex Biotec Ltd. Catalogue 2014, 2014, URL, https://docplayer.net/1077036-Kivex-biotec-ltd-catalogue.html.
Kivex Biotec Ltd. Catalogue 2013, 2013, URL, Kivex Biotec Ltd. Catalogue 2013, 2013, URL.
Kivex Biotec Ltd. Catalogue Sep. 2008, 2008, URL, http://medial.mediasolution.ez/data/files/medial/download/katalogy/k_systems/katalog_k_systems.pdf.
Kivex Biotec Ltd. Catalogue Jul. 2006, 2006, URL, http://www.instrumentalpasteur.com.ar/descargas/k-systems_catalogue2006.pdf.
The First Office Action from the Chinese Patent Office for Chinese Application No. CN 201680065390.8 dated Jul. 24, 2020 (with English Translation).
The Chinese Office Action for Chinese Application No. CN 201680065390.8, dated Feb. 20, 2021 (With English Translation).
Chinese Decision of Rejection for Chinese Application No. CN 201680065390.8 dated Sep. 14, 2021 (with English Translation).

* cited by examiner

«LAMINAR AIR FLOW WORKSTATION WITH TEMPERATURE CONTROL»

FIELD OF INVENTION

The present invention relates to a laminar air flow workstation, and the use of the workstation for handling and/or microscopy of biological materials, such as tissue, embryos, and stem cells, as well as the use of the workstation for microbiological safety workstation in accordance with ISO/EN 12469.

BACKGROUND OF INVENTION

Laminar air flow workstations, also denoted benches or cabinets, are used for safely working with materials that may be contaminated, such as contaminated with pathogens, or for handling materials that must be protected from exposure to the surroundings. For example when examining biological material, such as tissue, embryos, and stem cells, exposure to the surrounding atmospheric environment and the surrounding temperature may be detrimental.

Depending on the level of personnel and environmental protection provided by the workstation, and the level of product protection provided by the workstation, different classes of workstations are defined. Laminar flow cabinets only provide product protection, whereas class II cabinets provide both product and personnel protection. Class II workstations may be further certified to various ISO standards, such as ISO 12469.

Conventional laminar air flow workstations operate by blowing a vertical laminar air flow of sterile and/or filtered air, over the samples that are being handled.

To enable temperature control of the samples to be handled, the samples may be placed on heating means such as a heat plate to maintain a desired temperature. In addition, or alternatively, the workstation may form a closed system with no direct access from the surrounding, and the air flow may be heated, whereby the temperature of the sample surface can be controlled precisely.

Large volumes of aft are used in closed workstations with heated air flow. Thus, during operation, the workstations are noisy due to the fans and pumps driving the large volumes, and the energy consumption of the workstation, and the heat loss to the surroundings, are significant. To remedy this, the air may be partially recycled. However, the efficiency and simplicity is significantly reduced for a closed workstation, as the sample handling within the workstation as well as the transfer of samples to and from the workstation, is complicated.

It is therefore desirable to provide a laminar air flow workstation which is easily accessible from the surroundings, but with reduced energy consumption and heat loss to the surroundings, and a precisely temperature controlled air flow.

SUMMARY OF INVENTION

It is a purpose of the present invention to provide a laminar air flow workstation and class II workstation, preferably with a level of ISO 12469 approval. It is furthermore an purpose of the invention to provide a workstation that is easily accessible from the surroundings, has improved temperature control, and where the workstation in operation has a reduced noise level.

In a first aspect, the present invention provides a laminar air flow workstation, comprising:

a working chamber 1 comprising a work table 2,
an air circulation system 3 comprising first heating means 4, and configured to circulate heated air in the workstation and direct a heated and temperature controlled air flow towards the work table 2,
wherein the working chamber comprises a front handling opening 6 in fluid connection with the surroundings 7, and configured such that the work table 2 can be accessed from the surroundings 7.

In a second aspect, the workstation according to the first aspect is used for handling and/or microscopy of biological materials, such as tissue, embryos and stem cells, and/or used for a microbiological safety workstation in accordance with ISO/EN 12469.

DESCRIPTION OF DRAWINGS

The invention will in the following be described in greater detail with reference to the accompanying drawings.

FIG. 2: shows an embodiment of a laminar air flow workstation according to the present invention, where the workstation further comprises an insulation layer 18 on the outer surfaces, an inlet filter 20a, and an outlet filter 19a.

DETAILED DESCRIPTION OF THE INVENTION

Figure 1:
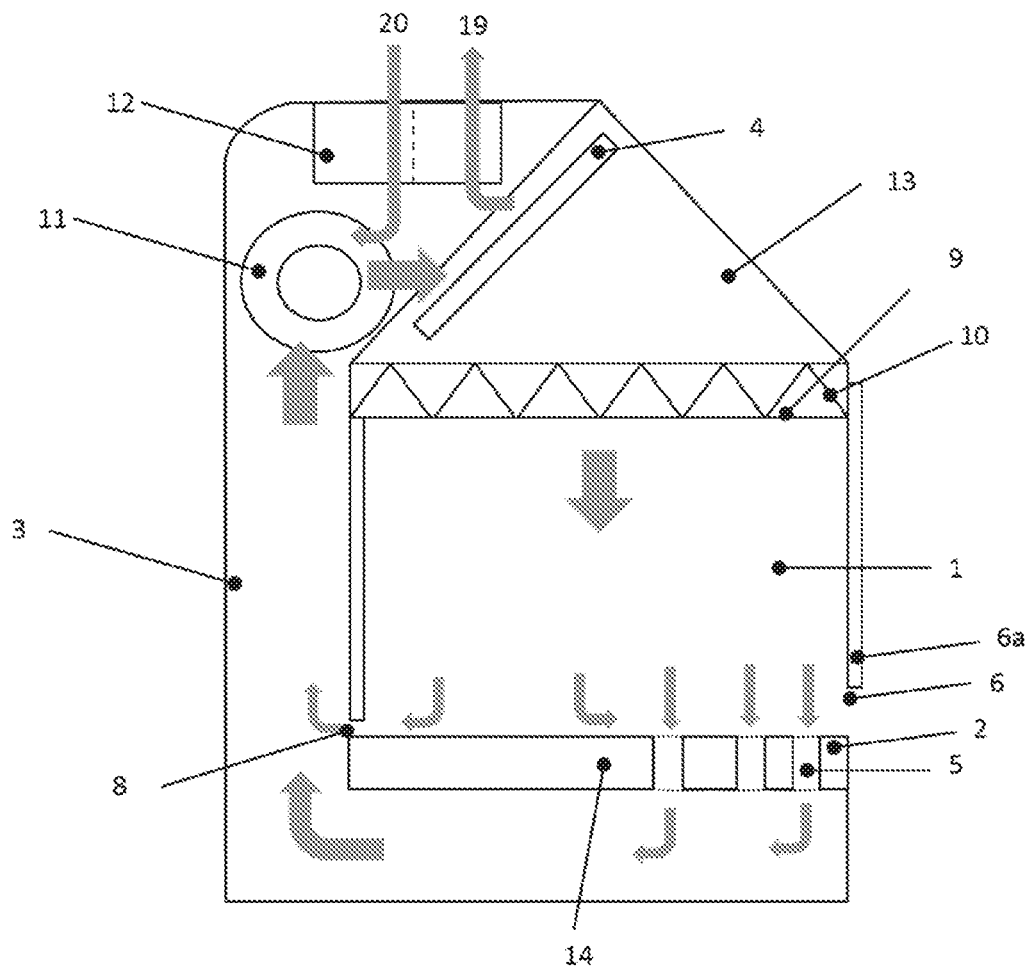
FIG. 1: shows an embodiment of a laminar air flow workstation according to the present invention.

FIG. 1 shows an embodiment of a laminar air flow workstation, also denoted LAF (Laminar Air Flow) cabinet. LAFs are in general used for laboratory work on materials, or samples that are temperature sensible, and/or require a clean environment, and which furthermore may constitute a health risk to human beings. Examples of such materials include biological materials, such as tissue, embryos and stem cells.

The workstation comprises a working chamber 1, a work table 2, and a front handling opening 6. The front handling opening opens towards the surroundings 7, and the size of the opening can be varied by sliding means configured such that a transparent front 6a can be displaced in an upward or downward direction.

The person(s) working at the workstation will be placed in front of the workstation, and can work with his/hers hands inside the working chamber, such as manipulate samples or operate instruments e.g. a microscope, as the working chamber and work table are visible through the transparent front 6a. Depending on the length of the workstation, one or more persons can work next to each other. Preferably, a workstation with a length of 122 cm (4 foot) is suitable for one person, and a workstation with a length of 183 cm (6 foot) is suitable for two persons.

It is advantageous that the samples and instruments to be handled can be placed in a stable position on the work table 2.

Thus, in an embodiment of the invention, the work table 2 is substantially horizontal.

Temperature Control of Sample

In FIG. 1, the temperature of the items placed on the work table 2 is controlled by directing a heated and temperature controlled air flow towards the work table, as shown by the arrows inside the working chamber 1.

For precise temperature control and minimal air resistance in the system, it is advantageous that the heated air flow is essentially laminar and/or perpendicular to the work table.

In an embodiment of the invention, the workstation is configured such that the direction of the air flow towards the work table 2 is essentially laminar and/or perpendicular to the work table.

When examining biological samples it advantageous that the temperature of the heated air flow is similar to the natural temperature of the biological sample.

Thus, in a further embodiment of the invention, the air flow directed towards the work table 2 is heated and configured to be controlled to be above 25° C., more preferably above 30° C., such as essentially 37° C.

The temperature of the items placed on the work table 2 may additionally be controlled by use of heating means 14 placed within or embedded in the work table 2, and/or placed on top of the work table 2. The heating means enable the work table to be partly heated, and configured to be temperature controlled, whereby the temperature of the items placed on the work table is controlled.

In a further embodiment of the invention, the work table 2 comprises second heating means 14, such that the work table is heated and configured to be temperature controlled.

When the heating means are embedded within the work table, the temperature controlled area of the work table surface will depend on the thermal conductivity properties of the work table material. The thermal conductivity of the material should be sufficient to transfer the thermal energy from the heating means to the surface of the work table, and to obtain a uniform temperature on an area of the surface of the work table.

Figure 6:
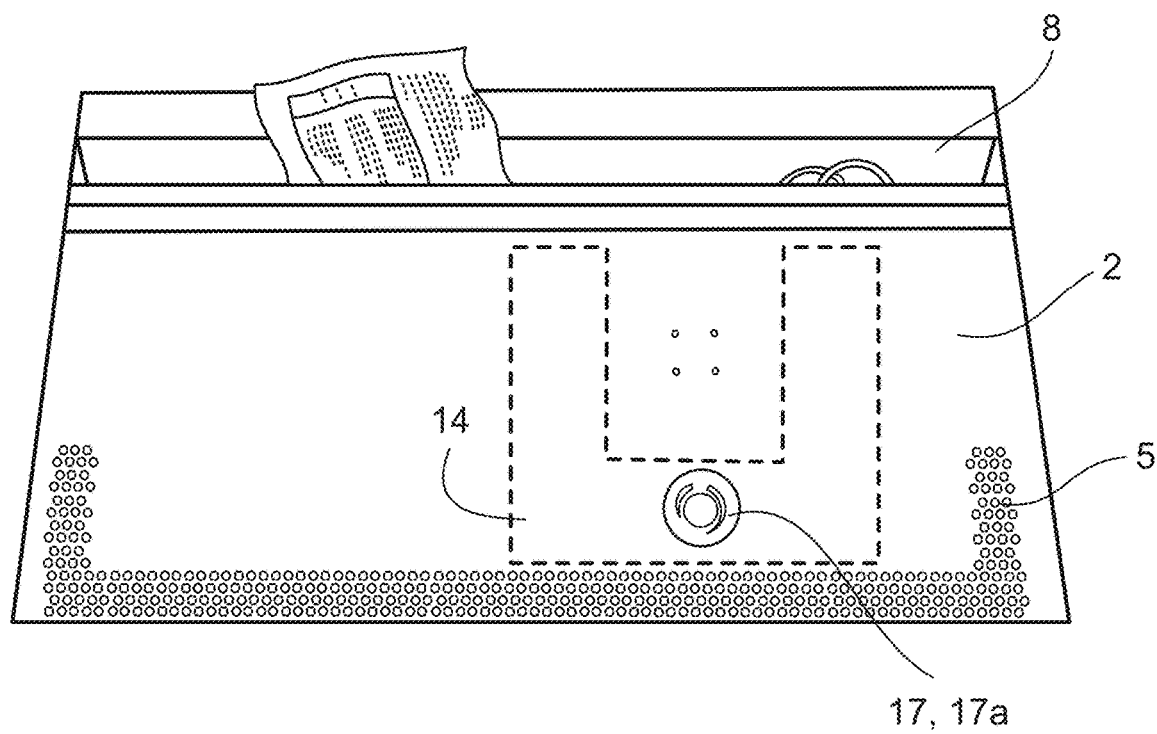
FIG. 6: shows a top view of an embodiment of a work table for a laminar air flow workstation according to the present invention, where the work table comprises second heating means 14, and where the position of the heating means are indicated.

In a further embodiment of the invention, the work table 2 comprises a material with thermal conductivity properties, such as a metal, an alloy, a composite, or any combinations thereof, FIG. 6 shows a top view of an embodiment of a work table, where the position of the heating means 14 are indicated by dashed lines. Thus, the dashed lines indicate the in-plane area of the heating means. Within at least the indicated surface area of the work table, the temperature of the work table surface is uniform, and can be controlled to be e.g. 37° C.

In a further embodiment of the invention, the in-plane area of the second heating means (14) constitute at least 25%, more preferably at least 35%, and most preferably at least 40 or 50% of the upper surface area of the work table 2.

Microscopy

Figure 3:
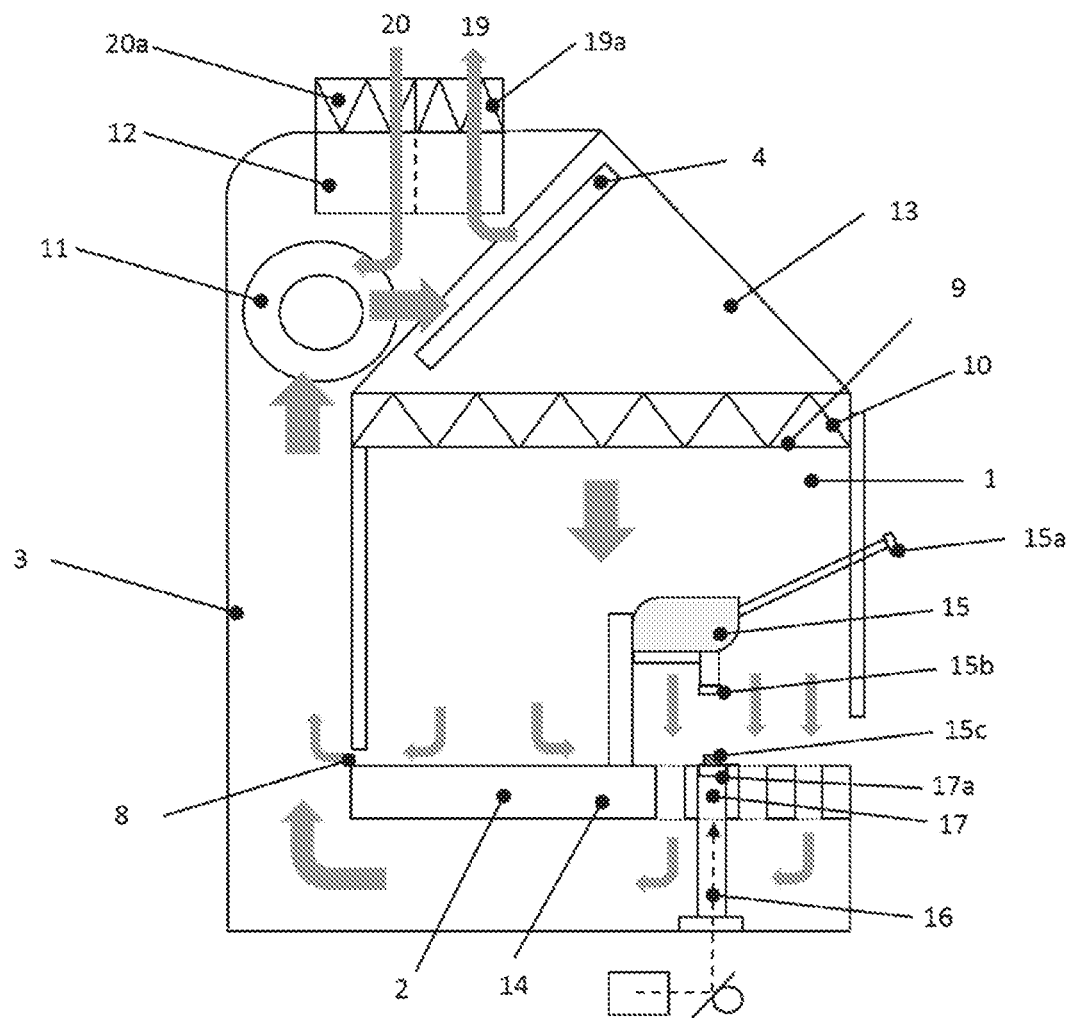
FIG. 3: shows an embodiment of a laminar air flow workstation according to the present invention, where the workstation is configured for optical microscopy, suitable for inspection of biological materials, such as living cells.

The samples to be handled within the workstation may be examined by microscopy, FIG. 3 shows an embodiment of a laminar air flow workstation, where the workstation comprises a microscope 15, and where the workstation is configured for carrying out microscopy.

In FIG. 3, the sample 15c to be examined by microscopy is placed on the work table 2, and the microscope lens 15b positioned above the sample. The sample object 15c is observed through the ocular 15a, which may be accessible from the surroundings, such as at the outer surface of the transparent front 6a.

The workstation may further be configured for optical transmission microscopy, where a beam of light is transmitted through the sample to be examined. FIG. 3 shows an embodiment of a workstation configured for transmission microscopy. The work table 2 comprises a transparent part 17, on top of which the sample 15c is placed. The sample 15c is transmitted by light from the light source 16 placed below the transparent part of the work table. To further ensure temperature control of the transmitted sample 15c, the sample may be placed on a transparent heated part 17a of the work table, such as heated glass.

In an embodiment of the invention, the workstation comprises a microscope 15, such as an optical microscope, and/or a light source 16. In a further embodiment, the workstation further comprises a transparent front 6a configured for microscopic inspection.

In a further embodiment of the invention, the work table 2 comprises a transparent part 17, and the light source 16 is optionally placed subjacent to the transparent part. In a further embodiment, the transparent part 17 comprises a transparent part configured to be heated 17a, such as a part made of glass. In a further embodiment, at least a part of the transparent part is heated and configured to be temperature controlled.

Air Circulation System

The air in the workstation is heated and circulated within the workstation by the air circulation system 3. Thus, all parts of the air circulation system are in fluid connection with each other. Embodiments of air circulation systems are shown in FIGS. 1-4.

Figure 2:
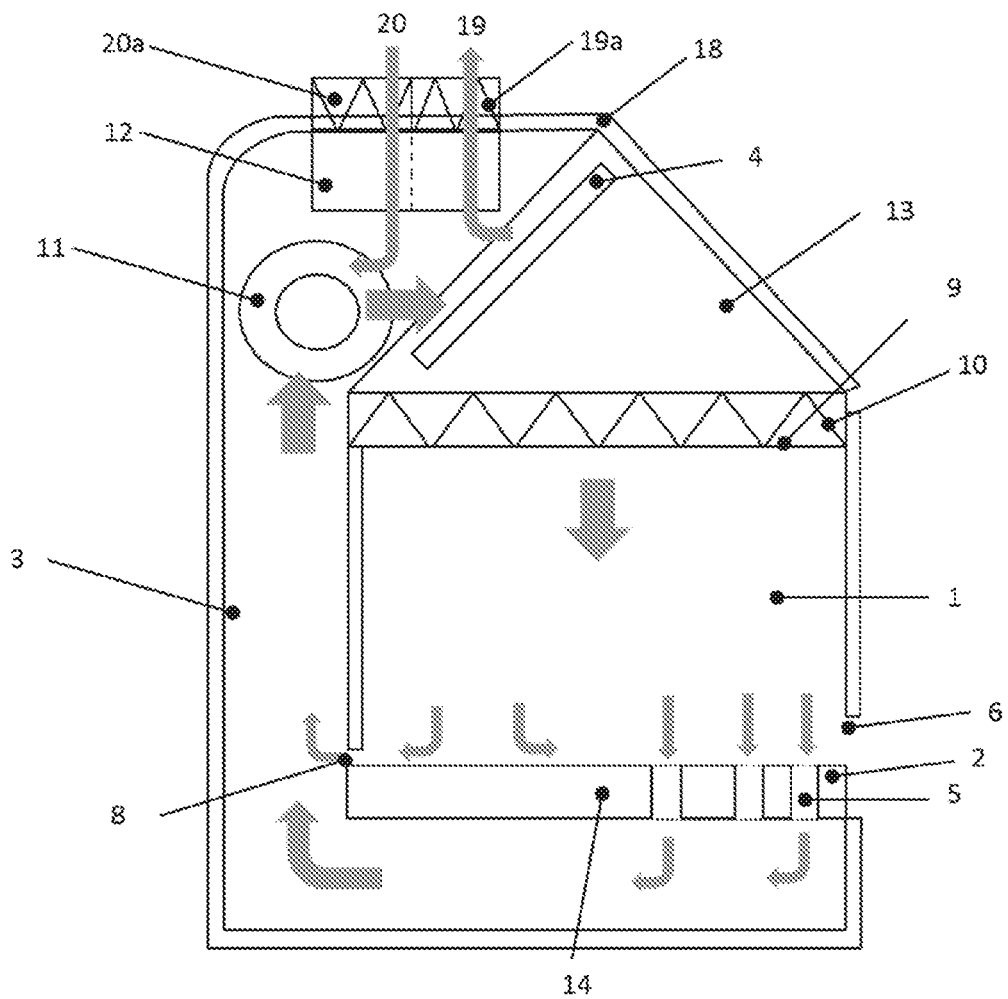

In the embodiments of FIGS. 1-3, air from the surroundings 7 is drawn into the air circulation system 3 at an air inlet 20. The entered air is then heated by being brought into contact with the first heating means 4. The first heating means 4 are configured to be temperature controlled, whereby the temperature of the entered and heated air can be controlled. Subsequently, the heated and temperature controlled air enters the working chamber 1, and is directed towards the work table 2. The table 2 comprises one or more ducts 5, and/or the working chamber comprises a rear duct 8, and the air flow directed towards the work table 2 is drawn through the duct(s). The air drawn through the duct(s) is subsequently either recycled, i.e. passed by the first heating means 4 and re-entered into the working chamber 1, or released to the surroundings 7 by an air outlet 19, or a combination thereof.

For continuous operation of the workstation, the amount of air released to the surroundings, is replaced by air from the surroundings entering at the air inlet 20.

Figure 4:
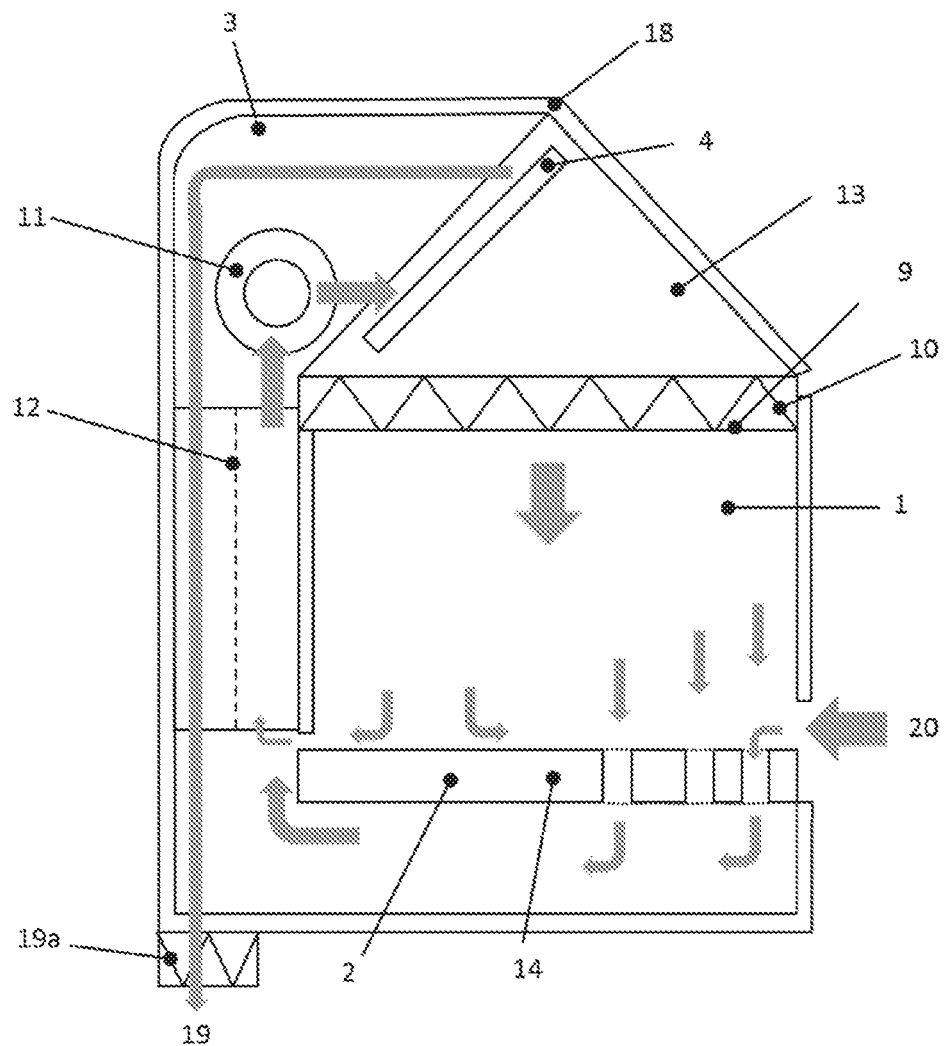
FIG. 4: shows an embodiment of a laminar air flow workstation according to the present invention, where air is drawn from the surroundings 7 into the workstation at the front handling opening 6.

An alternative embodiment of the air circulation system 3 is shown in FIG. 4. In this embodiment, the air is drawn from the surroundings 7 into the workstation at the front handling opening 6. The entered air is subsequently drawn through the duct(s) 5 of the work table 2, and brought into contact with the first heating means 4 and circulated to the working chamber 1 in similarly manner as in FIGS. 1-3.

In an embodiment of the invention, the front handling opening 6 comprises the air inlet 20.

The air circulation system 3, and implicitly the air entering/exiting the air circulation system, may be operated by use of an air flow generator 11. In an embodiment of the invention, the air circulation system 3 comprises an air flow generator 11, such as a fan. In a further embodiment, the air flow generator 11 is configured to control the air flows within the air circulation system 3.

To minimize the amounts of contaminants entering the air circulation system 3 at the air inlet 20, and exiting the air circulation system 3 at the air outlet 19, the inlet and/or outlet may comprise filtering means as illustrated in FIGS. 2-4.

In an embodiment of the invention, the workstation comprises an air inlet 20, and an air outlet 19, wherein the air inlet optionally comprises an inlet filter 20a, and the air outlet optionally comprises an outlet filter 19a.

The air circulation system 3 may further be operated by use of an air flow generator 11 in combination with a pressure chamber 13, or pressure box, where the pressure box is a part of the air circulation system with overpressure, or positive pressure. Optionally, the first heating means 4 are placed inside the pressure chamber as illustrated in FIGS. 1-4.

In an embodiment of the invention, the air circulation system 3 further comprises a pressure chamber 13, which in combination with the air flow generator 11 is configured to control the air flows within the air circulation system 3.

Energy Consumption

To minimize the energy consumption of the workstation, and the size of the air flows passing from the workstation to and from the surroundings, it is advantageous that part of the air circulated in the workstation is recycled.

In an embodiment of the invention, the air circulation system 3 is configured to recycle at least a part of the circulated air. In a further embodiment, at least 70%, more preferably at least 80%, and most preferably at least 90% of the circulated air is recycled. In a further embodiment, the amount of recycled air is controlled by flow control means, such as valves, slides, or throttles.

To further minimize the heat loss from the workstation and to the surroundings, all or some of the outer surfaces of the workstation may be completely or partly covered by an insulating material 18. FIGS. 2 and 4 show embodiments of workstations comprising an insulating layer 18 on the outer surfaces.

In an embodiment of the invention, the workstation further comprises an insulation layer 18 on one or more outer surface(s).

The energy consumption and heat loss may be further reduced by the use of heat exchanging means 12, whereby air entering at the inlet 20 from the surroundings 7, are partly heated by the air released from the workstation and to the surroundings 7. Embodiments of workstations comprising heat exchanging means 12 are illustrated in FIGS. 1-4.

By use of a cross heat exchanger as heat exchanging means 12, it was seen possible to heat the air entering at the inlet 20 with up to 10° C. For example, air entering at the inlet 20 with a temperature corresponding to the surroundings of 22° C., was heated to 29° C., while the air released from the workstation decreased in temperature from 37° C. to 30° C.

In an embodiment of the invention, the air circulation system further comprises heat exchanging means 12. In a further embodiment, the heat exchanging means 12 are selected from the group consisting of: heat exchanger, heat pump, and any combinations thereof. In a preferred embodiment, the heat exchanging means 12 is a cross heat exchanger.

In a further embodiment of the invention, the heat exchanging means 12 are configured to exchange air between the air circulation system 3 and air with essentially the same temperature as the surroundings 7.

Depending on the configuration of the air circulation system 3, the heat exchanging means 12 may be placed differently in the workstation. For the configuration embodied in FIGS. 1-3, where the air enters the workstation at the separate inlet 20, the heat exchanging means 12 are placed in the vicinity of the inlet 20, or on the top of the workstation.

In this embodiment of the invention, the heat exchanging means are configured to exchange heat between air flowing from the inlet 20 to the air flow generator 11, and air flowing from the pressure chamber 13 to the outlet 19.

For the configuration of the air circulation system 3 embodied in FIG. 4, where the air enters the workstation at the front handling opening 6,20, the heat exchanging means 12 are placed in the vicinity of the rear of the workstation, or at a distance from the inlet 20.

Thus, in another embodiment of the invention, the heat exchanging means are configured to exchange heat between air flowing from the pressure chamber 13 to the outlet 19, and air flowing from the part of the air circulation system placed below the worktable 2 to the air flow generator 11.

Work Table

By the term "work table" as used herein is meant a three-dimensional rectangle, or a box-shaped or hyper rectangular, component. The work table comprises an upper surface, where the work is carried out by a user, and the lower surface, which is the surface on the opposite side of the box. The other surfaces of the box comprise the edges of the work table. The work table front is the part of the work table in the vicinity of the front handling opening, and the work table rear is at the opposite edge, i.e. the part of the work table in the rear of the workstation.

By the term "in-plane" is meant an orientation parallel to the upper surface, and by the term "cross-plane" is meant an orientation perpendicular to the upper surface, and e.g., parallel to one of the edges.

Figure 5:
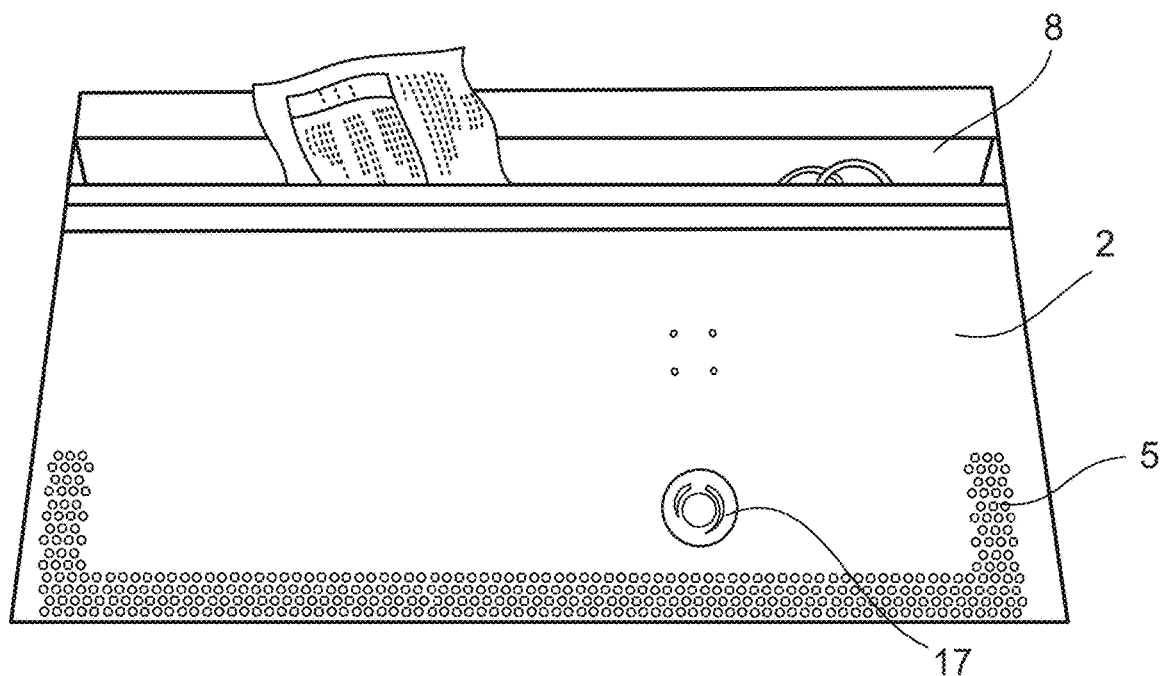
FIG. 5: shows a top view of an embodiment of a work table for a laminar air flow workstation according to the present invention.

FIG. 5 shows an embodiment of a work table seen from a top view, showing the work table upper surface. The work table is seen to comprise a larger rear duct 8, and a multiple of smaller ducts 5 which are oriented cross-plane of the work table, and placed along the front edge, and partly the two side edges, of the work table.

The air flow resistance, and therefore also the noise, of the workstation is dependent on the duct(s) of the work table 5 and the duct(s) of the workstation 8. To minimize the energy consumption of the workstation, it is advantageous that the duct(s) are configured to minimize the air flow resistance within the air circulation system 3.

In an embodiment of the invention, the work table 2 further comprises one or more ducts 5, such that at least part of the air flow directed towards the work table can be drawn through the duct(s).

In a further embodiment, the one or more ducts 5 extend from an upper surface of the work table, and to a lower surface of the work table, and/or to an edge surface of the work table. In a further embodiment, the one or more ducts 5 are oriented cross-plane of the work table. In a further embodiment, the one or more ducts 5 are positioned adjacent to one or more edge(s) of the work table.

In a further embodiment of the invention, the geometry of the one or more ducts 5 are selected from the group consisting of: cylindrical, columnar, polygonal columnar, such as hexagonal columnar, and any combinations thereof.

In a further embodiment of the invention, the in-plane area of the one or more ducts 5 constitute at least 5%, more preferably at least 10% or 20%, and most preferably at least 25% of the upper surface area of the work table 2.

To further minimize the air flow resistance of the air circulation system, the working chamber may in addition to the duct(s) of the work table 2, comprise one or more rear duct(s) 8. The rear duct(s) may be placed in the rear of the working chamber 1, such as comprised within the work table 2 in the rear part of the work table as illustrated in FIG. 5.

In an embodiment of the invention, the working chamber comprises one or more rear duct(s) 8 such that at least a part of the air flow directed towards the work table 2 can be drawn through the rear duct(s).

The energy consumption of the workstation may further be improved if the majority of the circulated air is drawn through the rear duct(s) 8, compared to the duct(s) 5 comprised in the work table.

This is particularly the case for the embodiments shown in FIGS. 1-3, where the risk of air entering from the surroundings 7 and into the working chamber 1 via the front handling opening 6, is reduced.

In an embodiment of the invention, the air flow drawn through the rear duct(s) 8 is larger than the air flow drawn through the one or more ducts (5).

Working Chamber

In the embodiments shown in FIGS. 1-4, the heated and temperature controlled air enters the working chamber 1, from the pressure chamber 13, through an opening 9, and is directed towards the work table 2.

To avoid contaminants entering the working chamber 1, filtering means 10 may be used such that the heated and temperature controlled air is filtered before entering the working chamber 1. The filter may for example be a High-Efficiency Particulate Arrestance (HEPA), where particles above a certain size are removed.

In an embodiment of the invention, the workstation further comprises a filter 10, such as a HEPA filter, or a filtered opening 9.

The filter 10 may further be positioned above the work table, and configured to affect the distribution of the air flow directed towards the work table 2.

In an embodiment of the invention, the filter 10 is positioned such that filtered air is directed into the working chamber 1. In another embodiment, the workstation comprises a filtered opening 9 in the air circulation system 3 located above the work table 2. In a further embodiment, the filtered opening 9 is configured to evenly distribute the heated air vertically downwardly within the working chamber 1 and towards the work table 2.

In some embodiments of the invention, such as the embodiments shown in FIGS. 1-3, it is advantageous that the amount of air entering from the surroundings 7 and into the working chamber 1 via the front handling opening 6, is minimized. The amount of air entering through the front handling opening 6 is determined by the pressure difference between the working chamber 1 and the surroundings 7. The pressure of the working chamber 1 is further determined by the ratio of air flowing into the working chamber through the filtered opening 9, and air drawn through the duct(s) 5,8.

Thus, in preferred embodiments, the air pressure in the working chamber 1 is essentially similar or slightly lower than the air pressure of the surroundings 7. More preferably, the pressure difference across the front handling opening 6 is zero, and no air enters the working chamber through the front handling opening.

In an embodiment of the invention, the air circulation system 3 is configured such that the pressure difference across the front handling opening 6, i.e. between the working chamber 1 and the surroundings 7, is essentially zero.

In a further embodiment, the workstation is configured such that the air flow through the filtered opening 9 is essentially similar or lower than the air flow drawn through the duct(s) 5,8, more preferably essentially similar.

In some embodiments of the invention, such as the embodiment shown in FIG. 4, the handling opening 6 is used as air inlet 20. For this to occur, there must be a significant pressure difference across the front handling opening 6, and the pressure in the working chamber 1 must be lower compared to the surroundings 7.

In an embodiment of the invention, the workstation is configured such that the pressure is significantly lower in the working chamber 1 compared to the surroundings 7.

REFERENCE NUMBERS

1—working chamber
2—work table
3—air circulation system
4—first heating means
5—ducts
6—front handling opening
6a—transparent front
7—surroundings
8—rear duct
9—filtered opening
10—filter
11—air flow generator
12—heat exchanging means
13—pressure chamber
14—second heating means
15—microscope
15a—occular
15b—lense
15c—sample
16—light source
17—transparent part of work table
17a—transparent heated part of work table
18—insulation layer
19—air outlet
19a—outlet filter
20—air inlet
20a—inlet filter

The invention claimed is:

1. A laminar air flow workstation, comprising:
a working chamber comprising a work table and a front handling opening, the front handling opening being in fluid communication with a surrounding environment and configured such that the work table is accessible from the surrounding environment;
a filter positioned to filter air directed into the working chamber; and
an air circulation system configured to circulate the air in the laminar air flow workstation and to direct a flow of the air towards the work table, the air circulation system comprising:
an air flow generator configured to control the flow of the air,
a pressure chamber disposed above the work table, and
a heating means disposed within the pressure chamber and positioned downstream of and laterally to the air flow generator,
wherein the heating means is spaced apart from the filter, positioned directly above the filter, and positioned upstream of the filter to heat the air after the air flows from the air flow generator and before the air contacts the filter and passes into the working chamber, such that the heating means, the air flow generator, and the pressure chamber together provide an operational configuration that heats and controls a temperature of the air.

2. The laminar air flow workstation according to claim 1, wherein the air in the flow directed towards the work table is heated and controlled to be above 25° C.

3. The laminar air flow workstation according to claim 1, wherein the flow of the air directed towards the work table is essentially laminar and/or is directed perpendicularly to the work table.

4. The laminar air flow workstation according to claim 1, wherein the heating means comprises a first heating means, and wherein the work table comprises a second heating means for heating and controlling a temperature of the work table.

5. The laminar air flow workstation according to claim 1, wherein the work table comprises a thermally conductive material.

6. The laminar air flow workstation according to claim 1, further comprising a microscope.

7. The laminar air flow workstation according to claim 6, further comprising a transparent front portion configured to permit inspection of the microscope, and wherein the work table comprises a transparent part disposed above a light source associated with the microscope.

8. The laminar air flow workstation according to claim 1, wherein the work table comprises one or more ducts through which at least part of the flow of the air directed towards the work table can be drawn.

9. The laminar air flow workstation according to claim 1, wherein the working chamber further comprises one or more rear ducts through which at least a part of the flow of the air directed towards the work table can be drawn.

10. The laminar air flow workstation according to claim 1, further comprising a filtered opening disposed in the air circulation system and above the work table and configured to evenly distribute the flow of the air vertically downward within the working chamber and towards the work table.

11. The laminar air flow workstation according to claim 1, wherein the air flow generator is further configured to control an air inflow and an air outflow at the air circulation system.

12. The laminar air flow workstation according to claim 11, wherein the air circulation system further comprises a heat exchanging means selected from a group comprising a heat exchanger, a heat pump, and any combinations thereof.

13. The laminar air flow workstation according to claim 12, wherein the heat exchanging means comprises a cross heat exchanger.

14. The laminar air flow workstation according to claim 12, wherein the pressure chamber, in combination with the air flow generator, is configured to further control the air inflow and the air outflow at the air circulation system.

15. The laminar air flow workstation according to claim 14, further comprising an air inlet comprising an inlet filter and an air outlet comprising an outlet filter.

16. The laminar air flow workstation according to claim 15, wherein the heat exchanging means is configured to exchange air between the air circulation system and air with essentially the same temperature as the surrounding environment.

17. The laminar air flow workstation according to claim 1, wherein the air circulation system is configured to recycle at least a part of the air that has been heated by the heating means.

18. The laminar air flow workstation according to claim 1, wherein the air circulation system is configured such that a pressure difference between an interior region of the working chamber and the surrounding environment, across the front handling opening, is essentially zero.

19. The laminar air flow workstation according to claim 1, wherein the laminar air flow workstation is configured such that a pressure is significantly lower in the laminar air flow workstation compared to a pressure of the surrounding environment.

\* \* \* \* \*